United States Patent
Matsuoka et al.

(10) Patent No.: US 9,890,725 B2
(45) Date of Patent: Feb. 13, 2018

(54) GAS SENSOR CONTROL DEVICE

(71) Applicant: DENSO CORPORATION, Kariya, Aichi-pref. (JP)

(72) Inventors: Mikiyasu Matsuoka, Kariya (JP); Shingo Nakata, Kariya (JP)

(73) Assignee: DENSO CORPORATION, Kariya (JP)

( * ) Notice: Subject to any disclaimer, the term of this patent is extended or adjusted under 35 U.S.C. 154(b) by 135 days.

(21) Appl. No.: 14/896,110

(22) PCT Filed: May 16, 2014

(86) PCT No.: PCT/JP2014/002596
§ 371 (c)(1),
(2) Date: Dec. 4, 2015

(87) PCT Pub. No.: WO2014/196131
PCT Pub. Date: Dec. 11, 2014

(65) Prior Publication Data
US 2016/0123262 A1 May 5, 2016

(30) Foreign Application Priority Data
Jun. 4, 2013 (JP) .................. 2013-117481

(51) Int. Cl.
*G01N 37/00* (2006.01)
*F02D 41/12* (2006.01)
(Continued)

(52) U.S. Cl.
CPC ....... *F02D 41/123* (2013.01); *F02D 41/1456* (2013.01); *F02D 41/1495* (2013.01);
(Continued)

(58) Field of Classification Search
CPC ............. G01N 33/0006; G01N 33/007; G01N 27/4163; F02D 41/222; F02D 41/1495; F02D 41/123; G01M 15/104
(Continued)

(56) References Cited

U.S. PATENT DOCUMENTS

| 7,751,966 B2 * | 7/2010 | Iwazaki | G01M 15/104 123/198 D |
| 9,664,640 B2 * | 5/2017 | Yamada | G01N 27/407 |

(Continued)

FOREIGN PATENT DOCUMENTS

| JP | 60-98141 | 6/1985 |
| JP | 61-118653 | 6/1986 |

OTHER PUBLICATIONS

International Search Report for PCT/JP2014/002596, dated Aug. 19, 2014, 2 pages.
(Continued)

*Primary Examiner* — Peter Macchiarolo
*Assistant Examiner* — Mohammed E Keramet-Amircolai
(74) *Attorney, Agent, or Firm* — Nixon & Vanderhye P.C.

(57) ABSTRACT

A constant current circuit is controlled to stop a constant current Ics (Ics=0) flowing between sensor electrodes of an oxygen sensor, in a period before the oxygen sensor becomes active, during a fuel cut of an engine, and after the engine stops. When an abnormality (for example, a failure) occurs in the constant current circuit, a sensor output equivalent to an output of the oxygen sensor of when the constant current circuit is controlled to stop the constant current Ics is different from a normal sensor output. An abnormality diagnosis is executed to determine a presence or absence of the abnormality in the constant current circuit depending on whether the output of the oxygen sensor is out of a predetermined normal range, in a period before the oxygen sensor becomes active, during a fuel cut of an engine, and after the engine stops (when the constant current circuit is controlled to stop the constant current Ics).

9 Claims, 10 Drawing Sheets

(51) Int. Cl.
    *F02D 41/14*     (2006.01)
    *F02D 41/22*     (2006.01)
    *G01N 27/406*     (2006.01)
    *G01M 15/10*     (2006.01)
    *G01N 33/00*     (2006.01)

(52) U.S. Cl.
    CPC ....... *F02D 41/1496* (2013.01); *F02D 41/222* (2013.01); *G01M 15/104* (2013.01); *G01N 27/4065* (2013.01); *G01N 33/007* (2013.01)

(58) Field of Classification Search
    USPC ......................................................... 73/1.06
    See application file for complete search history.

(56) References Cited

U.S. PATENT DOCUMENTS

| | | | | |
|---|---|---|---|---|
| 2008/0185289 A1* | 8/2008 | Matsuoka | ......... | G01N 27/4065 204/425 |
| 2012/0031078 A1* | 2/2012 | Sakamoto | ......... | F02D 41/1466 60/277 |
| 2012/0031168 A1* | 2/2012 | Sakamoto | ......... | F01N 11/00 73/23.33 |
| 2012/0034569 A1* | 2/2012 | Sakamoto | ......... | G01N 15/0656 431/76 |
| 2012/0043205 A1* | 2/2012 | Matsuoka | ......... | G01N 27/407 204/410 |
| 2013/0192210 A1* | 8/2013 | Nakano | ......... | F02D 41/1439 60/276 |
| 2013/0192211 A1* | 8/2013 | Nakano | ......... | F01N 9/005 60/276 |
| 2013/0206596 A1* | 8/2013 | Katsurahara | ......... | G01N 27/407 204/424 |
| 2013/0298658 A1* | 11/2013 | Kanenari | ......... | B60C 23/0494 73/146.4 |
| 2015/0025778 A1 | 1/2015 | Matsuoka et al. | | |

OTHER PUBLICATIONS

Written Opinion of the ISA for PCT/JP2014/002596, dated Aug. 19, 2014, 7 pages.

\* cited by examiner

GAS SENSOR CONTROL DEVICE

CROSS REFERENCE TO RELATED APPLICATION

This application is the U.S. national phase of International Application No. PCT/JP2014/002596 filed 16 May 2014, which designated the U.S. and claims priority to JP Patent Application No. 2013-117481 filed 4 Jun. 2013, the entire contents of each of which are hereby incorporated by reference.

TECHNICAL FIELD

The present disclosure relates to a gas sensor control device provided with a gas sensor that detects a concentration of a predetermined component contained in a detected gas.

BACKGROUND ART

In an internal-combustion engine vehicle, an emission gas purification catalyst is disposed to an exhaust pipe and an emission gas sensor that detects an air-fuel ratio of an emission gas or whether the emission gas is rich or lean is disposed upstream of the catalyst or both upstream and downstream of the catalyst. An emission gas purification ratio of the catalyst is increased by applying feedback control to an air-fuel ratio on the basis of an output of the emission gas sensor. Herein, the emission gas sensor is equivalent to an air-fuel ratio sensor or an oxygen sensor.

In the emission gas sensor, such as an oxygen sensor, when an air-fuel ratio of an emission gas varies between rich and lean, a sensor output varies in response to a variance of an actual air-fuel ratio with a lag in some cases.

In view of the circumstances, the gas sensor has a sensor element in which a solid electrolyte layer is disposed between sensor electrodes as disclosed, for example, in Patent Literature 1 (JP S60-98141 A). The gas sensor is equivalent to an oxygen sensor and the sensor electrodes have a reference electrode and an oxygen electrode. Output characteristics of the gas sensor are changed by controlling a current flowing from the reference electrode to the oxygen electrode using a current supply portion.

PRIOR ART LITERATURES

Patent Literature

Patent Literature 1: JP S60-98141 A

When an abnormality (for example, a failure) occurs in the current supply portion that controls a current flowing between the sensor electrodes, the output characteristics of the gas sensor cannot be changed properly and a control (for example, air-fuel ratio feedback control) on the basis of an output of the gas sensor cannot be performed properly, either. Hence, when an abnormality occurs in the current supply portion, it is necessary to detect the abnormality promptly.

The inventor considered a configuration for a system for an abnormality diagnosis including a constant current supply portion that changes the output characteristics of the gas sensor by controlling a constant current flowing between the sensor electrodes, and the system switches a current value flowing between the sensor electrodes when a predetermined abnormality diagnosis executing condition is established (for example, while a fuel cut is being executed) and determines the presence or absence of an abnormality in the constant current supply portion on the basis of outputs of the gas sensor before and after the switching.

However, in order to execute the abnormality diagnosis as above, it is necessary to detect an output of the gas sensor before the current value is switched, then to switch the current value flowing between the sensor electrodes, and to detect an output of the gas sensor after the current value is switched. Hence, a time required for the abnormality diagnosis tends to extend. Further, frequency of the occurrence is likely to increase for a case where an abnormality diagnosis cannot be completed while the abnormality diagnosis executing condition is established. In addition, the abnormality diagnosis may possibly have an adverse influence on other controls (for example, rich injection control performed to neutralize the catalyst immediately after the fuel cut ends).

SUMMARY OF INVENTION

The present disclosure has an object to provide a gas sensor control device not only capable of detecting an abnormality in a constant current supply portion that changes output characteristics of a gas sensor, but also capable of shortening a time required for an abnormality diagnosis.

According to an aspect of the present disclosure, the gas sensor control device includes a gas sensor that detects a concentration of a predetermined component contained in a detected gas using a sensor element in which a solid electrolyte body is disposed between a pair of sensor electrodes, a constant current supply portion that changes output characteristics of the gas sensor by controlling a constant current flowing between the sensor electrodes, and an abnormality diagnosis portion that executes an abnormality diagnosis to determine presence or absence of an abnormality in the constant current supply portion on the basis of an output of the gas sensor when the constant current supply portion is controlled to stop the constant current or maintain the constant current at a predetermined value.

When an abnormality (for example, a failure) occurs in the constant current circuit, and when the constant current circuit is controlled to stop the constant current Ics flowing between the sensor electrodes of the oxygen sensor or to maintain the constant current Ics at a predetermined value, an output of the oxygen sensor differs from a normal output. In the present embodiment, an abnormality diagnosis to determine the presence or absence of an abnormality in the constant current circuit is executed depending on whether an output of the oxygen sensor is out of a predetermined normal range when the constant current circuit is controlled to stop the constant current Ics or to maintain the constant current Ics at the predetermined value. Hence, the presence or absence of an abnormality in the constant current circuit can be determined with accuracy. Consequently, when an abnormality occurs in the constant current circuit, the abnormality can be detected promptly. Moreover, it is not necessary to switch the constant current Ics flowing between the sensor electrodes when an abnormality diagnosis is executed. Hence, in comparison with a case where an abnormality diagnosis is executed on the basis of outputs of the oxygen sensor before and after the current value is switched, a time required for an abnormality diagnosis can be shorter. Accordingly, an abnormality diagnosis can be completed more frequently while the abnormality diagnosis executing condition is established. In addition, an adverse influence on other controls can be prevented.

BRIEF DESCRIPTION OF DRAWINGS

The above and other objects and advantages of the present disclosure will be more readily apparent from the following detailed description made with reference to the accompanying drawings. In the drawings.

DESCRIPTION OF EMBODIMENTS

Hereinafter, an embodiment as a concrete example to implement the present disclosure will be described.

Figure 1:
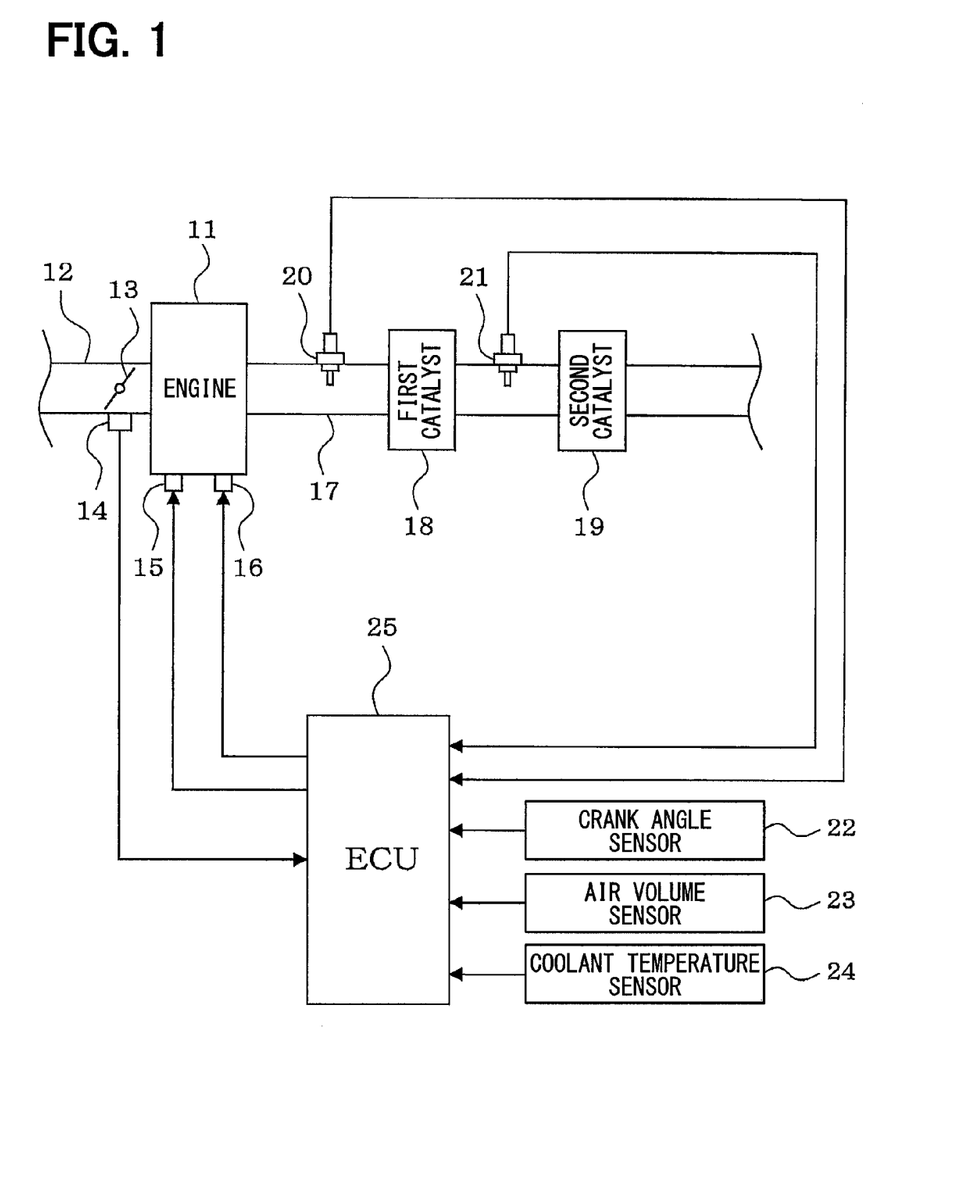
FIG. 1 is a view schematically showing a configuration of an engine control system according to an embodiment of the present disclosure.

Firstly, a schematic configuration of an overall engine control system will be described according to FIG. 1.

An intake pipe 12 of an engine 11, which is an internal combustion engine, is provided with a throttle valve 13 that is adjusted to a suitable degree of opening by a motor or the like and a throttle opening sensor 14 that detects a degree of opening (throttle opening) of the throttle valve 13. Fuel injection valves 15 are attached to respective cylinders of the engine 11 to inject fuel into cylinders or into intake ports of the cylinders. Sparking plugs 16 are attached to the respective cylinders in a cylinder head of the engine 11. An air-fuel mixture in each cylinder is ignited with a spark discharge by the corresponding sparking plug 16.

An exhaust pipe 17 of the engine 11 is provided with a first catalyst 18 and a second catalyst 19, such as a three-way catalyst that purifies CO, HC, $NO_x$ and so on in an emission gas. As a first gas sensor, an air-fuel ratio sensor 20 (linear A/F sensor) that outputs a linear air-fuel ratio signal corresponding to an air-fuel ratio of the emission gas is provided upstream of the first catalyst 18. Herein, an air-fuel ratio of the emission gas is also referred to as an excess air ratio $\lambda$. Further, as a second gas sensor, an oxygen sensor 21 ($O_2$ sensor) is provided downstream of the first catalyst 18 (more specifically, between the first catalyst 18 and the second catalyst 19). An output voltage of the oxygen sensor 21 inverts depending on whether an air-fuel ratio of the emission gas is rich or lean with respect to a theoretical air-fuel ratio. Herein, the theoretical air-fuel ratio is also referred to as a stoichiometric air-fuel ratio.

The present engine control system is provided with various sensors, such as a crank angle sensor 22 that outputs a pulse signal each time a crank shaft (not shown) of the engine 11 rotates a predetermined crank angle, an air volume sensor 23 that detects an intake air volume of the engine 11, and a coolant temperature sensor 24 that detects a coolant temperature of the engine 11. A crank angle and an engine speed are detected on the basis of an output signal of the crank angle sensor 22.

Outputs of the various sensors are inputted into an electronic control unit (ECU) 25. The ECU 25 is chiefly formed of a microcomputer 26 and controls a fuel injection amount, ignition timing, throttle opening (intake air volume) and the like according to an engine operation state by running various engine control programs pre-stored in a storage medium, such as an internal ROM.

When a predetermined execution condition for air-fuel ratio F/B control is established, the ECU 25 performs a main F/B control to correct an air-fuel ratio (fuel injection amount) by F/B on the basis of an output of the air-fuel ratio sensor 20 for an air-fuel ratio of an emission gas on the upstream side of the first catalyst 18 to coincide with a target air-fuel ratio. Further, the ECU 25 performs a sub-F/B control to correct a target air-fuel ratio on the upstream side of the first catalyst 18 or correct a F/B correction amount or a fuel injection amount in the main F/B control on the basis of an output of the oxygen sensor 21 for an air-fuel ratio of the emission gas on the downstream side of the first catalyst 18 to coincide with a control target value (for example, theoretical air-fuel ratio). Herein, F/B stands for feedback.

A configuration of the oxygen sensor 21 will now be described according to FIG. 2.

The oxygen sensor 21 has a sensor element 31 of a cup-like structure. In practice, the sensor element 31 is entirely stored in an unillustrated housing or element cover and disposed in the exhaust pipe 17 of the engine 11.

In the sensor element 31, a solid electrolyte layer 32 equivalent to a solid electrolyte body is formed to have a U-shaped cross section. The solid electrolyte layer 32 is provided with an exhaust-side electrode layer 33 on an outer surface and with an atmosphere-side electrode layer 34 on an inner surface. The solid electrolyte layer 32 is executed from an oxygen-ion conducting sintered oxide executed of a solid solvent in which CaO, MgO, $Y_2O_3$, $Yb_2O_3$, or the like as a stabilizer is dissolved in $ZrO_2$, $HfO_2$, $ThO_2$, $Bi_2O_3$, or the like. Both of the exhaust-side electrode layer 33 and the atmosphere-side electrode layer 34 are executed of a high catalytically active noble metal, such as platinum, and porous chemical plating or the like is applied to the surfaces. The exhaust-side electrode layer 33 and the atmosphere-side electrode layer 34 are a pair of sensor electrodes opposite to each other. An internal space surrounded by the solid electrolyte layer 32 defines an atmospheric chamber 35. A heater 36 is stored inside the atmospheric chamber 35. The heater 36 has a sufficient heating capacity to activate the sensor element 31 and an entire of the sensor element 31 is heated by heating energy of the heater 36. An activating temperature of the oxygen sensor 21 is, for example, approximately 350 to 400° C. The interior of the atmospheric chamber 35 is maintained at a predetermined oxygen concentration by introducing air.

The sensor element 31 is in an atmosphere of emission on an outer side of the solid electrolyte layer 32 near the exhaust-side electrode layer 33 and in an atmosphere of air on an inner side of the solid electrolyte layer 32 near the atmosphere-side electrode layer 34. An electromotive force is generated between the electrode layers 33 and 34 according to a difference of oxygen concentrations (difference of oxygen partial pressures) between the two atmospheres. In short, different electromotive forces are generated in the sensor element 31 depending on whether an air-fuel ratio is rich or lean. Consequently, the oxygen sensor 21 outputs an electromotive force signal corresponding to an oxygen concentration (that is, air-fuel ratio) of an emission gas.

Figure 3:
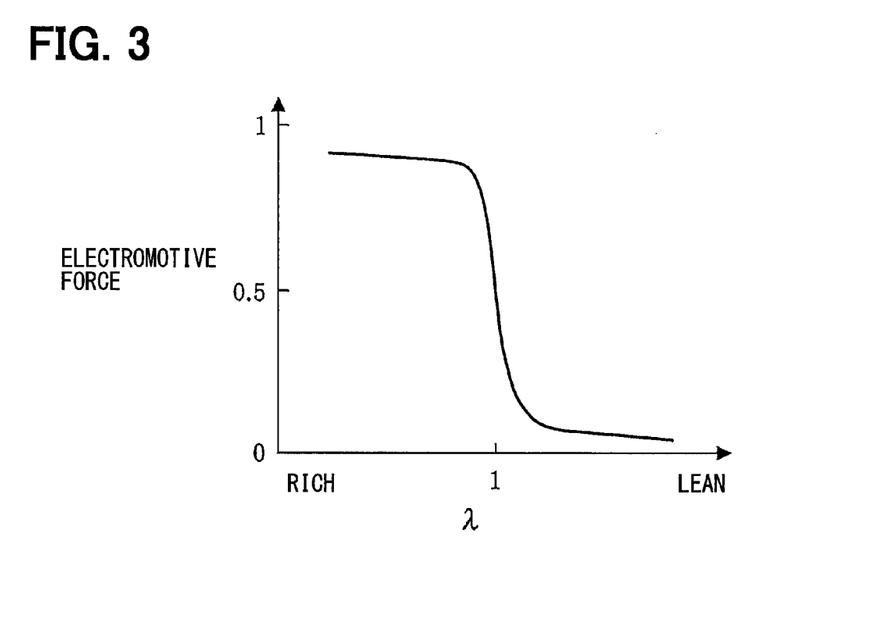
FIG. 3 is an electromotive force characteristic chart showing a relation between an air-fuel ratio of an emission gas and an electromotive force of the sensor element.

As is shown in FIG. 3, the sensor element 31 has characteristics that different electromotive forces are generated depending on whether an air-fuel ratio is rich or lean with respect to a theoretical air-fuel ratio (excess air ratio $\lambda=1$) and that the electromotive force varies abruptly at or near the theoretical air-fuel ratio. More specifically, an electromotive force of the sensor element 31 is about 0.9 V when fuel is rich whereas an electromotive force of the sensor element 31 is about 0 V when fuel is lean.

Figure 2:
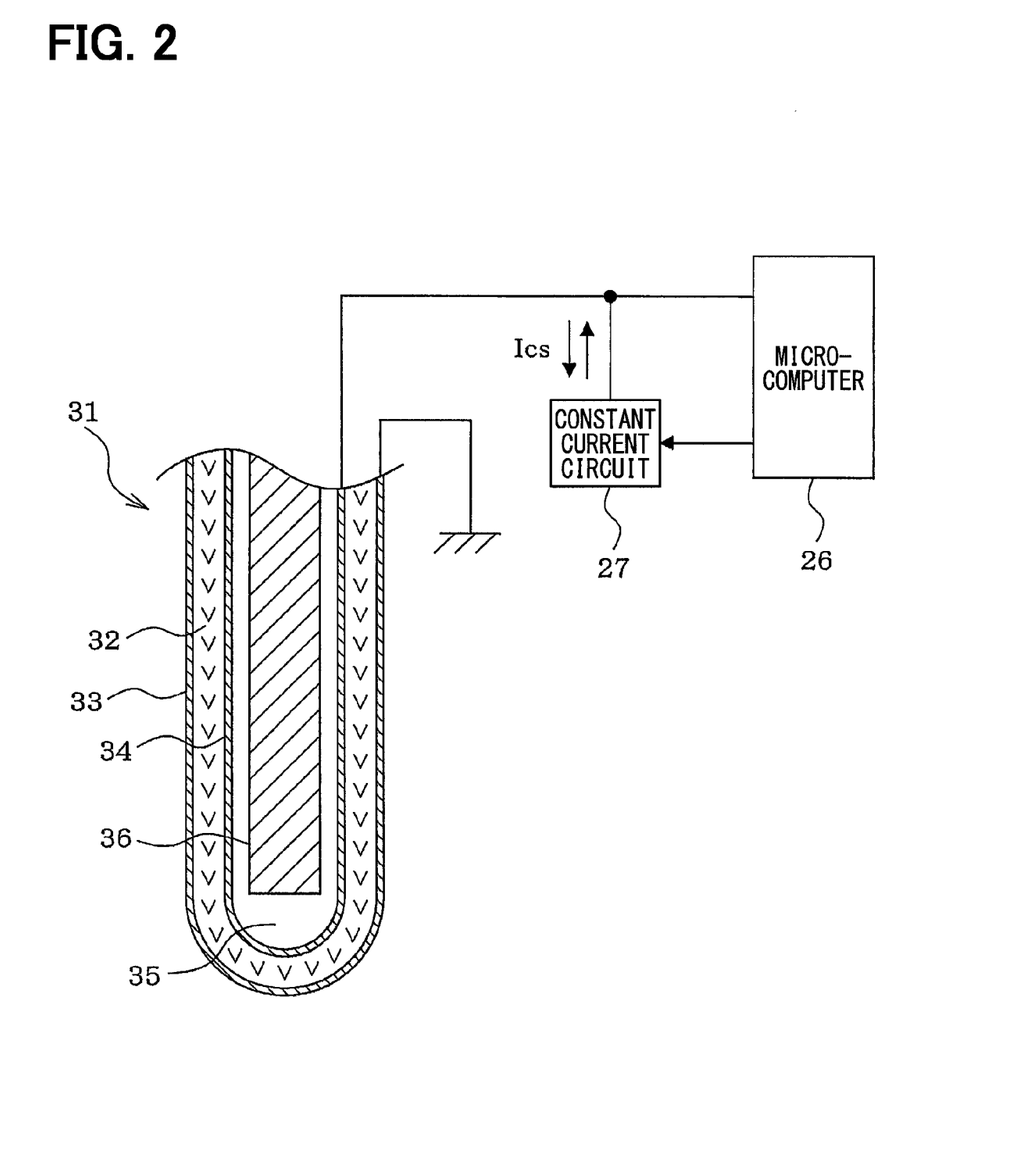
FIG. 2 is a sectional view showing a configuration of a sensor element.

As is shown in FIG. 2, the exhaust-side electrode layer 33 of the sensor element 31 is grounded and the microcomputer 26 is connected to the atmosphere-side electrode layer 34. When an electromotive force is generated in the sensor element 31 according to an air-fuel ratio (oxygen concentration) of the emission gas, a sensor detection signal comparable to the generated electromagnetic force is outputted to the microcomputer 26. It may be configured in such a manner that the sensor detection signal (voltage) inputted into the microcomputer 26 is offset in a plus direction with respect to an electromotive force of the sensor element 31 for the sensor detection signal inputted into the microcomputer 26 to vary within a region of plus values even when a constant current is supplied (when the output characteristics of the oxygen sensor 21 are changed).

The microcomputer 26 is provided, for example, inside the ECU 25, and calculates an air-fuel ratio on the basis of the sensor detection signal. The microcomputer 26 may calculate an engine speed and an intake air volume on the basis of detection results of the various sensors specified above.

While the engine 11 is in operation, an actual air-fuel ratio of an emission gas varies from time to time and may vary alternately, for example, between rich and lean. When the oxygen sensor 21 has low detection responsiveness to such a variance of the actual air-fuel ratio, the low detection responsiveness may possibly have an influence on the engine performance. For example, an amount of $NO_x$ in an emission gas may increase more than intended when the engine 11 is running under a high load.

Figure 4:
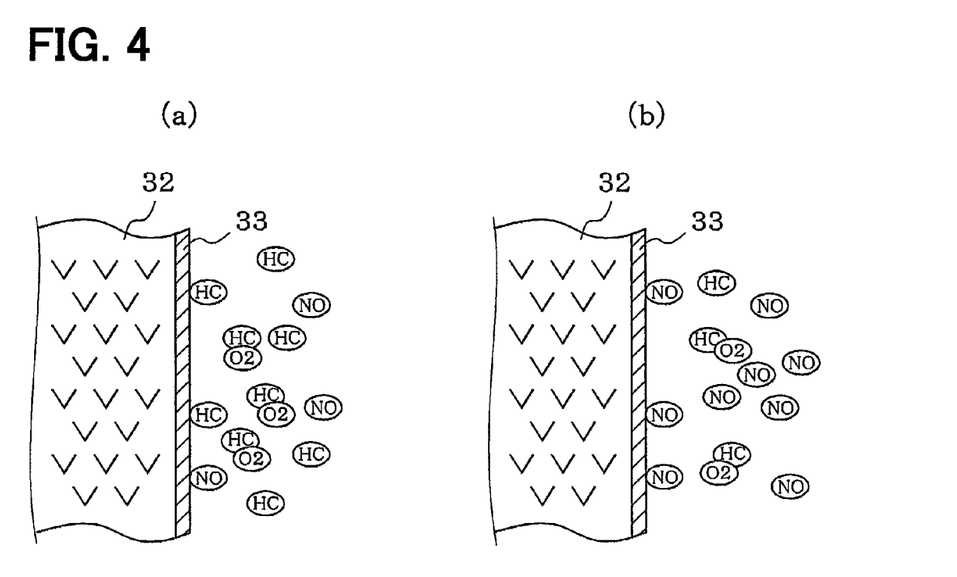
FIG. 4 illustrates views schematically showing states of gas components on the periphery of the sensor element.

A description will now be given to detection responsiveness of the oxygen sensor 21 when an actual air-fuel ratio varies between rich and lean. When an actual air-fuel ratio (actual air-fuel ratio on the downstream side of the first catalyst 18) of an emission gas exhausted from the engine 11 varies between rich and lean, a component composition of the emission gas varies. An output of the oxygen sensor 21 varies in response to the varied air-fuel ratio (that is, responsiveness of a sensor output) with a lag due to residual components of the emission gas immediately before the variance. More specifically, as is shown in FIG. 4(a), HC or the like, which is a rich component, remains on the periphery of the exhaust-side electrode layer 33 immediately after the air-fuel ratio varies from rich to lean, and the rich component interferes with a reaction of a lean component ($NO_x$ or the like) at the sensor electrodes. Consequently, responsiveness of a lean output as the oxygen sensor 21 deteriorates. On the contrary, when an actual air-fuel ratio varies from lean to rich, as is shown in FIG. 4(b), $NO_x$ or the like, which is a lean component, remains on the periphery of the exhaust-side electrode layer 33 immediately after the air-fuel ratio varies from lean to rich, and the lean component interferes with a reaction of the rich component (HC or the like) at the sensor electrodes. Consequently, responsiveness of a rich output as the oxygen sensor 21 deteriorates.

Figure 5:
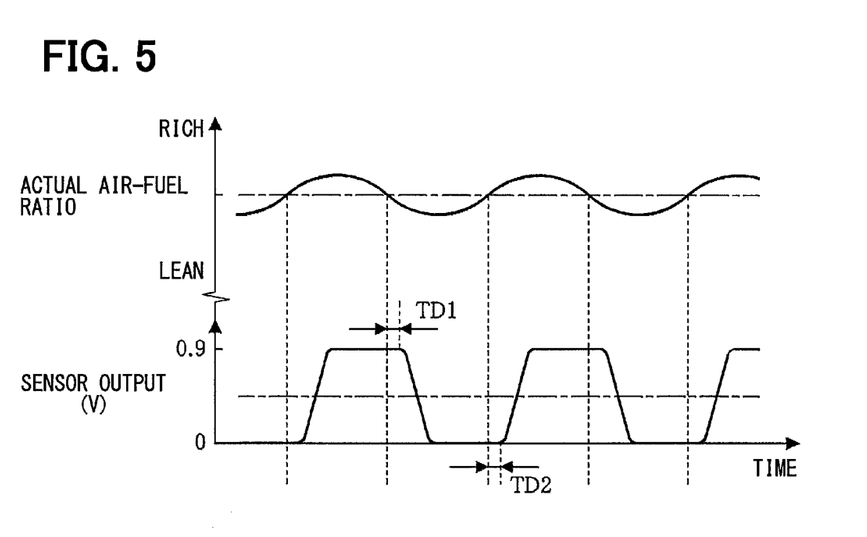
FIG. 5 is a time chart used to describe a behavior of a sensor output.

A variance of an output of the oxygen sensor 21 will be described using the time chart of FIG. 5. Referring to FIG. 5, when an actual air-fuel ratio varies between rich and lean, a sensor output equivalent to an output of the oxygen sensor 21 varies between a rich gas detection value (for example, 0.9 V) and a lean gas detection value (for example, 0 V) in response to a variance of the actual air-fuel ratio. It should be noted, however, that the sensor output varies in response to a variance of the actual air-fuel ratio with a lag. In FIG. 5, when the actual air-fuel ratio varies from rich to lean, the sensor output varies in response to a variance of the actual air-fuel ratio with a lag TD1 and when the actual air-fuel ratio varies from lean to rich, the sensor output varies in response to a variance of the actual air-fuel ratio with a lag TD2.

In the present embodiment, as shown in FIG. 2, a constant current circuit 27 as a constant current supply portion is connected to the atmosphere-side electrode layer 34. The ECU 25 (microcomputer 26) controls a supply of a constant current Ics by the constant current circuit 27 for a current to flow between a pair of the sensor electrodes 33 and 34 in a predetermined direction. Consequently, the ECU 25 (microcomputer 26) changes detection responsiveness of the oxygen sensor 21 by changing the output characteristics. Herein, the microcomputer 26 sets a direction and an amount of the constant current Ics flowing between a pair of the sensor electrodes 33 and 34 and controls the constant current circuit 27 for the set constant current Ics to flow.

More specifically, the constant current circuit 27 supplies the atmosphere-side electrode layer 34 with the constant current Ics in either a forward or backward direction. Moreover, the constant current circuit 27 is capable of adjusting a constant current amount variably. In short, the microcomputer 26 controls the constant current Ics variably under PWM control or the like. The constant current circuit 27 adjusts the constant current Ics according to a duty signal outputted from the microcomputer 26 and the constant current Ics after the current amount adjustment flows between the sensor electrodes 33 and 34.

In the present embodiment, the constant current Ics flowing from the exhaust-side electrode layer 33 to the atmosphere-side electrode layer 34 is defined as a minus constant current (−Ics) and the constant current Ics flowing from the atmosphere-side electrode layer 34 to the exhaust-side electrode layer 33 is defined as a plus constant current (+Ics).

Figure 6:
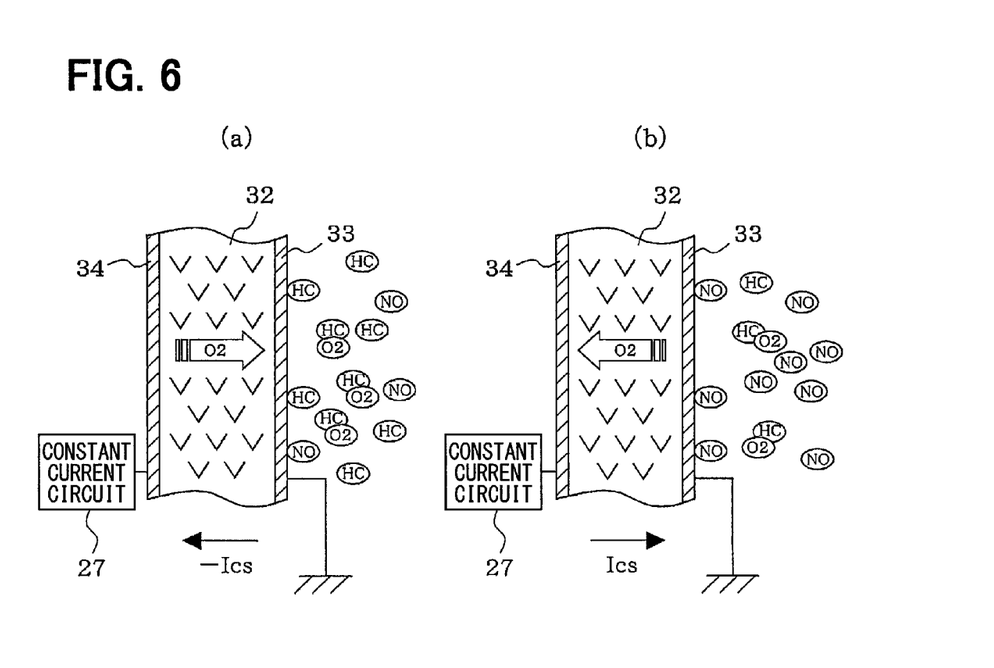
FIG. 6 illustrates views schematically showing states of gas components on the periphery of the sensor element through which a constant current flows.

For example, when increasing lean sensitivity equivalent to detection responsiveness to a variance of an actual air-fuel ratio from rich to lean, as is shown in FIG. 6(a), the constant current Ics (minus constant current Ics) is flowed so as to supply oxygen from the atmosphere-side electrode layer 34 to the exhaust-side electrode layer 33 through the solid electrolyte layer 32. Herein, oxygen supplied from the atmosphere side to the exhaust side promotes an oxidation reaction of the rich component (HC) present (remaining) on the periphery of the exhaust-side electrode layer 33. The rich component can be thus removed immediately. Accordingly, the lean component ($NO_x$) reacts more readily in the exhaust-side electrode layer 33. Consequently, responsiveness of a lean output of the oxygen sensor 21 is improved.

When increasing rich sensitivity equivalent to detection responsiveness to a variance of an actual air-fuel ratio from lean to rich, as is shown in FIG. 6(b), the constant current Ics (plus constant current Ics) is flowed so as to supply oxygen from the exhaust-side electrode layer 33 to the atmosphere-side electrode layer 34 through the solid electrolyte layer 32. Herein, oxygen supplied from the exhaust side to the atmosphere side promotes a reduction reaction of the lean component ($NO_x$) present (remaining) on the periphery of the exhaust-side electrode layer 33. The lean component can be thus removed immediately. Accordingly, the rich component (HC) reacts more readily in the exhaust-side electrode layer 33. Consequently, responsiveness of a rich output of the oxygen sensor 21 is improved.

Figure 7:
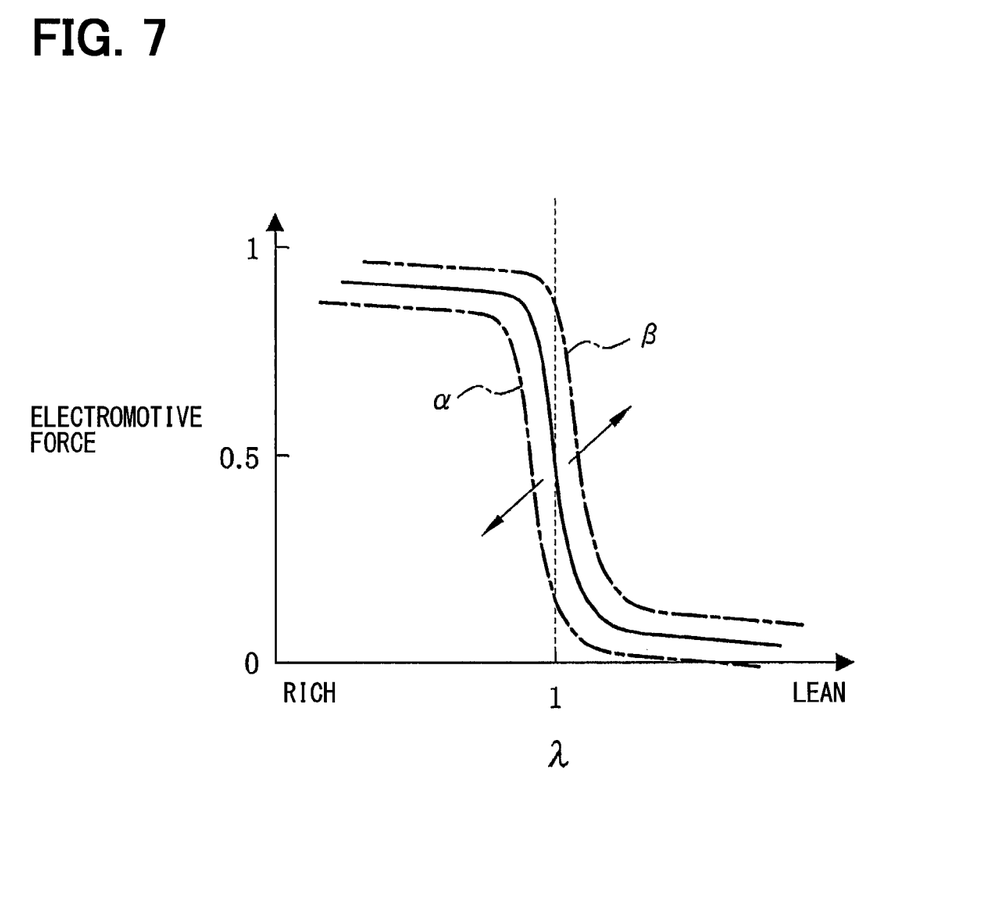
FIG. 7 is an output characteristic chart of an oxygen sensor when lean sensitivity or rich sensitivity is increased.

FIG. 7 is a view showing electromotive force characteristics equivalent to the output characteristics of the oxygen sensor 21 when increasing the lean sensitivity equivalent to detection responsiveness to a variance of an actual air-fuel ratio from rich to lean and when increasing the rich sensitivity equivalent to detection responsiveness to a variance of an actual air-fuel ratio from lean to rich.

In a case as shown in FIG. 6(a) where the lean sensitivity equivalent to detection responsiveness to a variance of an actual air-fuel ratio from rich to lean is increased, when the minus constant current Ics is flowed so as to supply oxygen from the atmosphere-side electrode layer 34 to the exhaust-side electrode layer 33 through the solid electrolyte layer 32 as described above, as is indicated by an alternate long and short dash line α of FIG. 7, an output characteristics line shifts to the rich side (more specifically, shifts to the rich side and an electromotive force decreasing side). Herein, the sensor output is a lean output even when an actual air-fuel ratio is in a rich region in the vicinity of the stoichiometric air-fuel ratio. That is to say, the lean sensitivity equivalent to detection responsiveness to a variance of an actual air-fuel ratio from rich to lean is increased as the output characteristics of the oxygen sensor 21.

Also, in a case as shown in FIG. 6(b) where the rich sensitivity equivalent to detection responsiveness to a variance of an actual air-fuel ratio from lean to rich, when the plus constant current Ics is flowed so as to supply oxygen from the exhaust-side electrode layer 33 to the atmosphere-side electrode layer 34 through the solid electrolyte layer 32 as described above, as is indicated by an alternate long and short dash line β of FIG. 7, the output characteristics line shifts to the lean side (more specifically, shifts to the lean side and an electromotive force increasing side). Herein, the sensor output is a rich output even when an actual air-fuel ratio is in a lean region in the vicinity of the stoichiometric air-fuel ratio. Consequently, the rich sensitivity equivalent to detection responsiveness to a variance of an actual air-fuel ratio from lean to rich is increased as the output characteristics of the oxygen sensor 21.

In the present embodiment, the ECU 25 (microcomputer 26) controls the constant current Ics flowing between the sensor electrodes 33 and 34 of the oxygen sensor 21 as below by executing a constant current control routine of FIG. 10.

The microcomputer 26 controls the constant current circuit 27 to stop the constant current Ics (set Ics=0) flowing between the sensor electrodes 33 and 34 of the oxygen sensor 21 in a period before the sensor element 31 of the oxygen sensor 21 becomes active, during a fuel cut to stop fuel injection of the engine 11, and after an engine stop (after the engine 11 stops).

During an engine operation (while the engine 11 is running), the ECU 25 (microcomputer 26) controls the constant current Ics flowing between the sensor electrodes 33 and 34 of the oxygen sensor 21 according to an engine operation state or the like. For example, when the engine 11 is cold, the ECU 25 (microcomputer 26) controls the constant current circuit 27 for the constant current Ics to flow in a direction to increase the rich sensitivity of the oxygen sensor 21. When the engine 11 is running under a high load, the microcomputer 26 controls the constant current circuit 27 for the constant current Ics to flow in a direction to increase the lean sensitivity of the oxygen sensor 21. During a rich injection control to neutralize the first catalyst 18 and the second catalyst 19 (cancel an excess-oxygen state) immediately after a fuel cut ends (that is, immediately after the fuel injection is restored), the microcomputer 26 controls the constant current circuit 27 for the constant current Ics to flow in a direction to decrease the rich sensitivity (in a direction to increase the lean sensitivity) of the oxygen sensor 21.

When an abnormality (for example, a failure) occurs in the constant current circuit 27 that controls the constant current Ics flowing between the sensor electrodes 33 and 34 of the oxygen sensor 21, the output characteristics of the oxygen sensor 21 cannot be changed properly. Hence, a control on the basis of an output of the oxygen sensor 21 (for example, the sub-F/B control) cannot be performed properly, either, which may possibly deteriorate an exhaust emission. In order to eliminate such a possibility, it is necessary to detect an abnormality promptly when the abnormality occurs in the constant current circuit 27.

Figure 11:
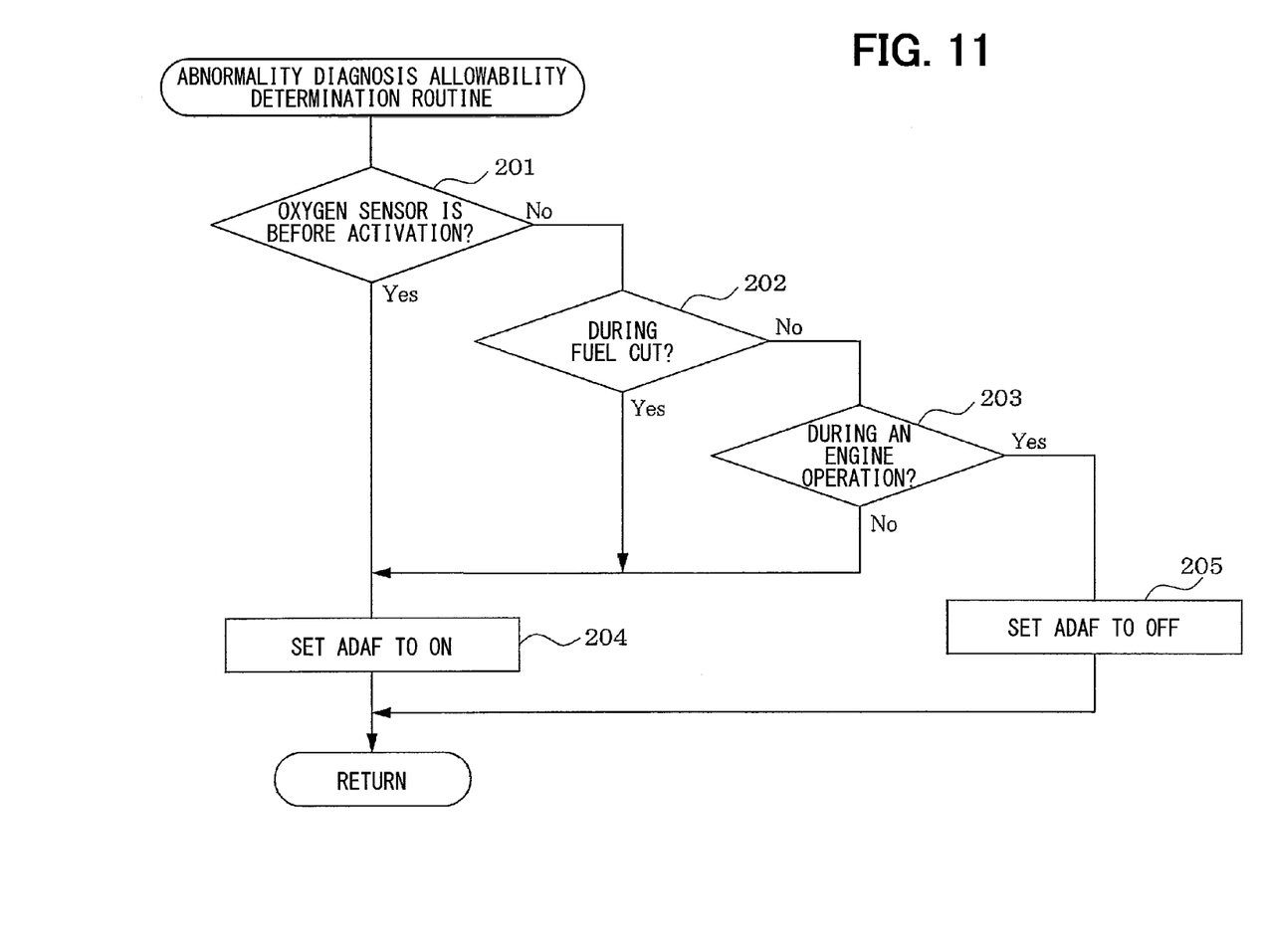
FIG. 11 is a flowchart depicting an abnormality diagnosis allowability determination routine.
Figure 12:
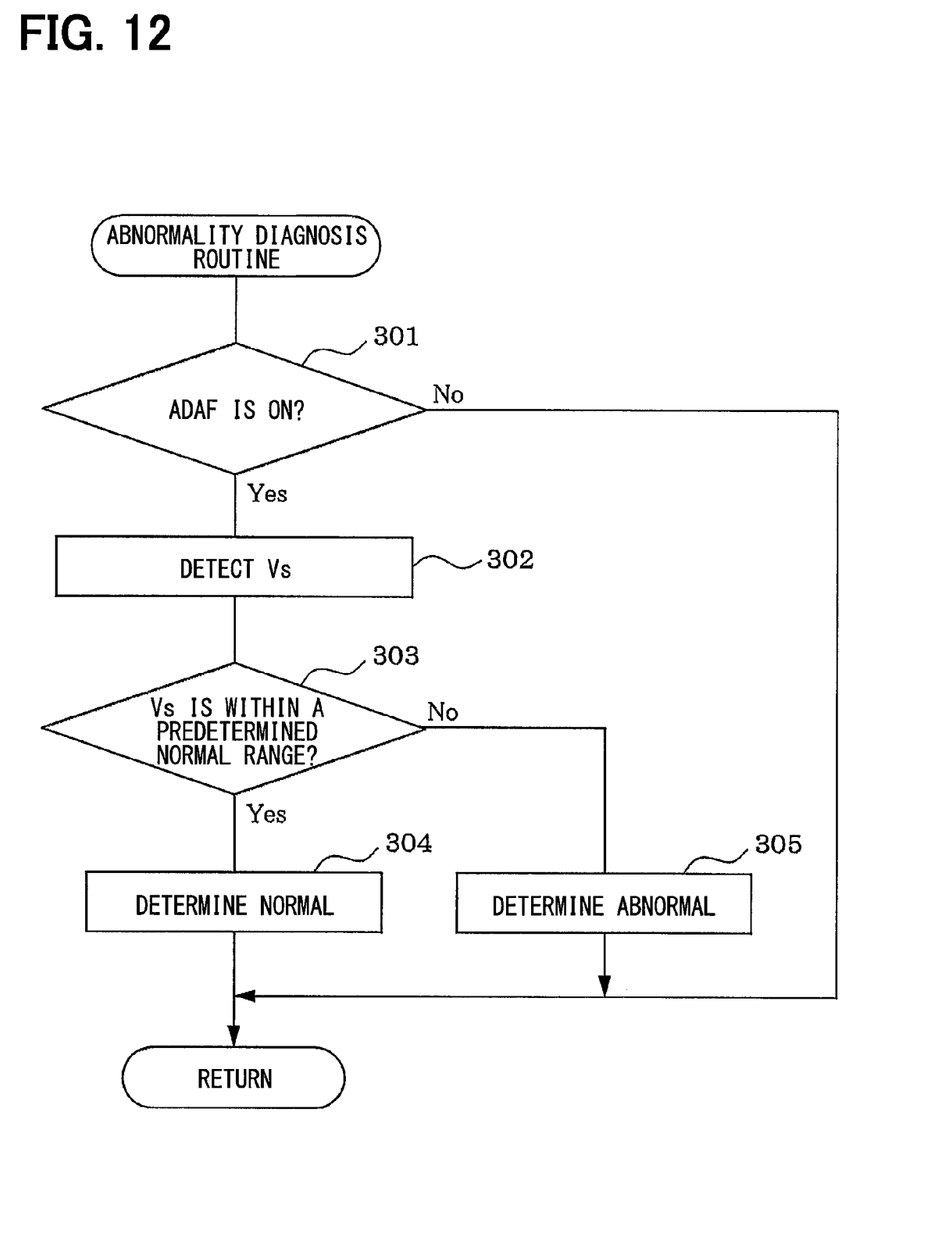
FIG. 12 is a flowchart depicting an abnormality diagnosis routine.

In the present embodiment, by executing respective abnormality diagnosis routines of FIG. 11 and FIG. 12, the ECU 25 (microcomputer 26) executes an abnormality diagnosis to determine the presence or absence of an abnormality (for example, a failure) in the constant current circuit 27 depending on whether an output of the oxygen sensor 21 is out of a predetermined normal range when the constant current circuit 27 is controlled to stop the constant current Ics (set Ics=0) flowing between the sensor electrodes 33 and 34 of the oxygen sensor 21.

Figure 8:
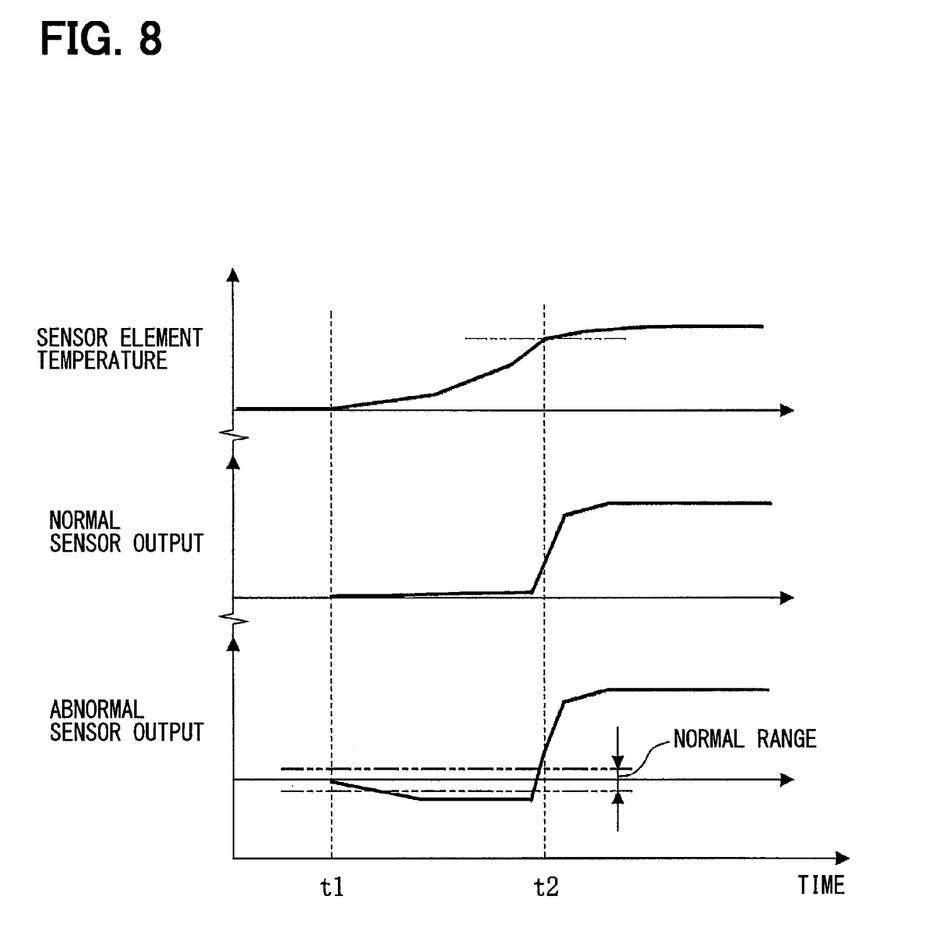
FIG. 8 is a time chart showing an abnormality diagnosis before activation of the oxygen sensor.
Figure 9:
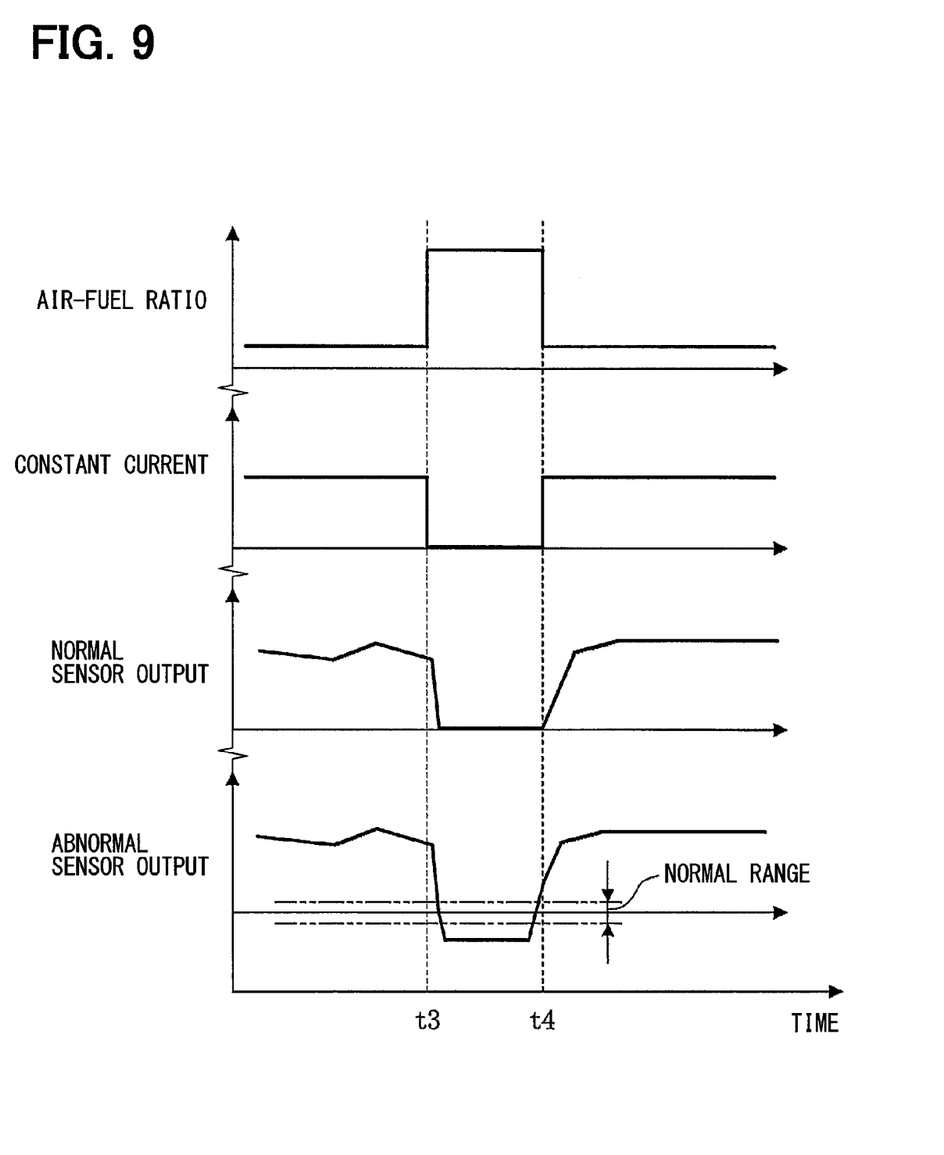
FIG. 9 is a time chart showing an abnormality diagnosis during a fuel cut.

As are shown in FIG. 8 and FIG. 9, when an abnormality (for example, a failure) occurs in the constant current circuit 27, a sensor output equivalent to an output of the oxygen sensor 21 of when the constant current circuit 27 is controlled to stop the constant current Ics is different from a normal sensor output. Hence, by executing an abnormality diagnosis to determine the presence or absence of an abnormality in the constant current circuit 27 depending on whether an output of the oxygen sensor 21 is out of the predetermined normal range using the ECU 25 (microcomputer 26) when the constant current circuit 27 is controlled to stop the constant current Ics, the presence or absence of an abnormality in the constant current circuit 27 can be determined with accuracy.

More specifically, as is shown in FIG. 8, the ECU 25 (microcomputer 26) detects an output of the oxygen sensor 21 before activation of the oxygen sensor 21 (for example, during a period from a time t1 when conduction of the heater 36 of the sensor element 31 is started to a time t2 when the sensor element 31 becomes active). The ECU 25 (microcomputer 26) executes an abnormality diagnosis to determine the presence or absence of an abnormality in the constant current circuit 27 depending on whether the detected output of the oxygen sensor 21 is out of the predetermined normal range. When configured in the manner above, the ECU 25 (microcomputer 26) is capable of executing an abnormality diagnosis on the constant current circuit 27 before activation of the oxygen sensor 21 when the constant current circuit 27 is controlled to stop the constant current Ics. Before activation of the oxygen sensor 21, an output of the oxygen sensor 21 is stable in the vicinity of a reference value (for example, 0 V) when the constant current circuit 27 is normal. Hence, the ECU 25 (microcomputer 26) is capable of executing an abnormality diagnosis on the constant current circuit 27 with accuracy on the basis of an output of the oxygen sensor 21.

Also, as is shown in FIG. 9, the ECU 25 (microcomputer 26) detects an output of the oxygen sensor 21 during a fuel cut (for example, in a period from a time t3 when a fuel cut starts to a time t4 when the fuel cut ends). The ECU 25 (microcomputer 26) executes an abnormality diagnosis to determine the presence or absence of an abnormality in the constant current circuit 27 depending on whether the detected output of the oxygen sensor 21 is out of the predetermined normal range. When configured in the manner above, the ECU 25 (microcomputer 26) is capable of executing an abnormality diagnosis on the constant current circuit 27 during a fuel cut when the constant current circuit 27 is controlled to stop the constant current Ics. During a fuel cut, an output of the oxygen sensor 21 is stable on the lean side (for example, in the vicinity of 0 V) when the constant current circuit 27 is normal. Hence, the ECU 25 (microcomputer 26) is capable of executing an abnormality diagnosis on the constant current circuit 27 with accuracy on the basis of an output of the oxygen sensor 21.

Further, the ECU 25 (microcomputer 26) detects an output of the oxygen sensor 21 after an engine stop and executes an abnormality diagnosis to determine the presence or absence of an abnormality in the constant current circuit 27 depending on whether the detected output of the oxygen sensor 21 is out of the predetermined normal range. When configured in the manner above, the ECU 25 (microcomputer 26) is capable of executing an abnormality diagnosis on the constant current circuit 27 after an engine stop when the constant current circuit 27 is controlled to stop the constant current Ics. After an engine stop, an output of the oxygen sensor 21 is stable on the lean side (for example, in the vicinity of 0 V) when the constant current circuit 27 is normal. Hence, the ECU 25 (microcomputer 26) is capable of executing an abnormality diagnosis on the constant current circuit 27 with accuracy on the basis of an output of the oxygen sensor 21.

Hereinafter, processing contents of the respective routines of FIG. 10 to FIG. 12 executed by the ECU 25 in the present embodiment will be described.

Figure 10:
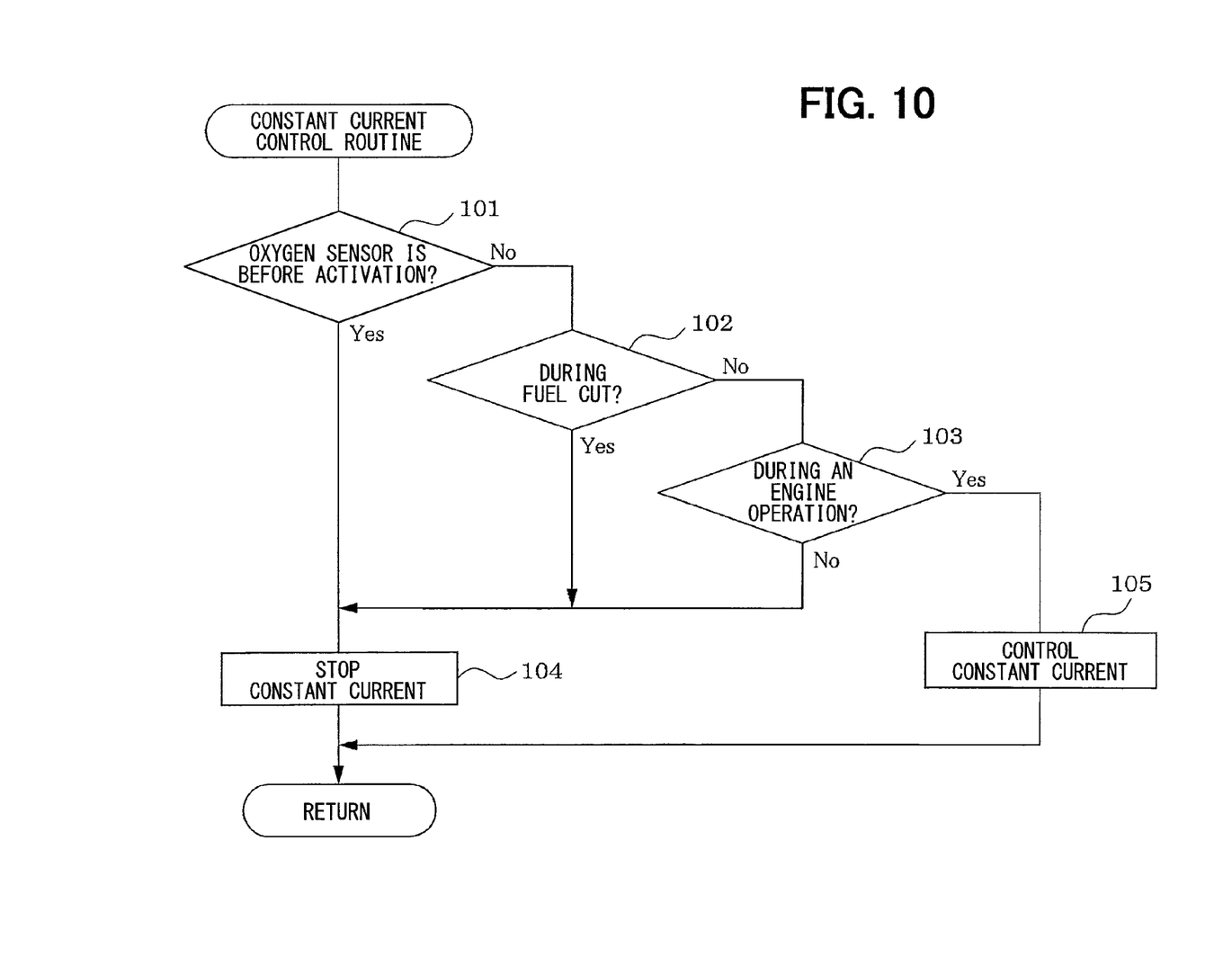
FIG. 10 is a flowchart depicting a constant current control routine.

The constant current control routine shown in FIG. 10 is repetitively executed in predetermined cycles while a power supply of the ECU 25 is ON and serves as a constant current control portion. When the constant current control routine is started, the ECU 25 firstly executes a determination in 101 as to whether the oxygen sensor 21 is before activation (before the sensor element 31 of the oxygen sensor 21 becomes active), for example, depending on whether element impedance of the sensor element 31 is at or above a predetermined value or whether a conducting time of the heater 36 is as long as or shorter than a predetermined time.

When the ECU 25 determines in 101 that the oxygen sensor 21 is before activation, the ECU 25 proceeds to 104. In 104, the ECU 25 controls the constant current circuit 27 to stop the constant current Ics (set Ics=0) flowing between the sensor electrodes 33 and 34 of the oxygen sensor 21.

When the ECU 25 determines in 101 that the oxygen sensor 21 is after activation, the ECU 25 proceeds to 102. In 102, the ECU 25 determines whether it is during a fuel cut (whether the fuel cut is being executed).

When the ECU 25 determines in 102 that it is during a fuel cut, the ECU 25 proceeds to 104. In 104, the ECU 25 controls the constant current circuit 27 to stop the constant current Ics flowing between the sensor electrodes 33 and 34 of the oxygen sensor 21.

When the ECU 25 determines in 102 that it is not during a fuel cut, the ECU 25 proceeds to 103. In 103, the ECU 25 determines whether it is during an engine operation (whether the engine 11 is operating).

When the ECU 25 determines in 103 that it is during an engine operation, the ECU 25 proceeds to 105. In 105, the ECU 25 controls the constant current Ics flowing between the sensor electrodes 33 and 34 of the oxygen sensor 21 according to the engine operation state and the like. For example, when the engine 11 is cold, the ECU 25 controls the constant current circuit 27 for the constant current Ics to flow in a direction to increase the rich sensitivity of the oxygen sensor 21. When the engine 11 is running under a high load, the ECU 25 controls the constant current circuit 27 for the constant current Ics to flow in a direction to increase the lean sensitivity of the oxygen sensor 21. During a rich injection control to neutralize the first catalyst 18 and the second catalyst 19 (to cancel an excess-oxygen state) immediately after the fuel cut ends (that is, immediately after the fuel injection is restored), the ECU 25 controls the constant current circuit 27 for the constant current Ics to flow in a direction to decrease the rich sensitivity (in a direction to increase the lean sensitivity) of the oxygen sensor 21.

When the ECU 25 determines in 103 that it is not during an engine operation (it is after an engine stop), the ECU 25 proceeds to 104. In 104, the ECU 25 controls the constant current circuit 27 to stop the constant current Ics flowing between the sensor electrodes 33 and 34 of the oxygen sensor 21.

An abnormality diagnosis allowability determination routine shown in FIG. 11 is repetitively executed in predetermined cycles while the power supply of the ECU 25 is ON. When the abnormality diagnosis allowability determination routine is started, the ECU 25 firstly executes a determination in 201 as to whether the oxygen sensor 21 is before activation.

When the ECU 25 determines in 201 that the oxygen sensor 21 is before activation, the ECU 25 proceeds to 204 on the grounds that an abnormality diagnosis executing condition is established. In 204, the ECU 25 sets an abnormality diagnosis allowance flag (ADAF) to ON (allowed state), which means that an abnormality diagnosis is allowed.

When the ECU 25 determines in 201 that the oxygen sensor 21 is after activation, the ECU 25 proceeds to 202. In 202, the ECU 25 determines whether it is during a fuel cut.

When the ECU 25 determines in 202 that it is during a fuel cut, the ECU 25 proceeds to 204 on the grounds that the abnormality diagnosis executing condition is established. In 204, the ECU 25 sets the abnormality diagnosis allowance flag to ON (allowed state), which means that an abnormality diagnosis is allowed. It may be configured in such a manner that the ECU 25 sets the abnormality diagnosis allowance flag to ON after an elapse of a predetermined time since the fuel cut started. The predetermined time referred to herein is equivalent to a time long enough for an output of the oxygen sensor 21 to be stable on the lean side.

When the ECU 25 determines in 202 that it is not during a fuel cut, the ECU 25 proceeds to 203. In 203, the ECU 25 determines whether it is during an engine operation.

When the ECU 25 determines in 203 that it is during an engine operation, the ECU 25 proceeds to 205 on the grounds that the abnormality diagnosis executing condition is not established. In 205, the ECU 25 resets the abnormality diagnosis allowance flag to OFF (inhibited state), which means that an abnormality diagnosis is inhibited.

When the ECU 25 determines in 203 that it is not during an engine operation (it is after an engine stop), the ECU 25 proceeds to 204 on the grounds that the abnormality diagnosis executing condition is established. In 204, the ECU 25 sets the abnormality diagnosis allowance flag to ON (allowed state), which means that an abnormality diagnosis is allowed. It may be configured in such a manner that the ECU 25 sets the abnormality diagnosis allowance flag to ON after an elapse of a predetermined time since the engine stop. The predetermined time referred to herein is equivalent to a time long enough for an output of the oxygen sensor 21 to be stable on the lean side.

An abnormality diagnosis routine shown in FIG. 12 is repetitively executed in predetermined cycles while the power supply of the ECU 25 is ON and serves as an abnormality diagnosis portion. When the abnormality diagnosis routine is started, the ECU 25 firstly executes a determination in 301 as to whether the abnormality diagnosis allowance flag is ON (allowed state) to determine the establishment of the abnormality diagnosis executing condition.

When the ECU 25 determines in 301 that the abnormality diagnosis allowance flag is OFF (inhibited state), the ECU 25 ends the abnormality diagnosis routine without executing the processing relating to an abnormality diagnosis in 302 and subsequent steps on the grounds that the abnormality diagnosis executing condition is not established.

When the ECU 25 determines in 301 that the abnormality diagnosis allowance flag is ON (allowed state), the ECU 25 executes the processing relating to the abnormality diagnosis in 302 and subsequent steps as below on the grounds that the abnormality diagnosis executing condition is established.

In 302, the ECU 25 firstly detects a current output of the oxygen sensor 21 as a diagnostic sensor output Vs. It may be configured in such a manner that the ECU 25 detects an output of the oxygen sensor 21 more than once and uses a mean value as the diagnostic sensor output Vs.

Subsequently, the ECU 25 executes a determination in 303 as to whether the diagnostic sensor output Vs is within a predetermined normal range. The normal range is set in reference to an output V0 of the oxygen sensor 21 when the constant current circuit 27 is normal while the abnormality diagnosis executing condition is established. For example, the normal range is set to a range from the output V0 of the oxygen sensor 21 in a normal state to a predetermined value γ [a range from (V0−γ) to (V0+γ)]. The normal range may be set separately for an abnormality diagnosis executed before activation of the oxygen sensor 21, for an abnormality diagnosis executed during a fuel cut, and for an abnormality diagnosis executed after an engine stop.

When the ECU 25 determines in 303 that the diagnostic sensor output Vs is within the normal range, the ECU 25 proceeds to 304. In 304, the ECU 25 determines that the constant current circuit 27 has no abnormality (is normal).

On the contrary, when the ECU 25 determines in 303 that the diagnostic sensor output Vs is not within the normal range (out of the normal range), the ECU 25 proceeds to 305. In 305, the ECU 25 determines the presence of an abnormality in the constant current circuit 27 (for example, the constant current circuit 27 is fixed in a current ON state). Herein, the ECU 25 sets an abnormality flag to ON and warns a driver, for example, by lighting or flashing a warning lamp (not shown) provided to an instrument panel at a driver's seat or by displaying a warning on a warning display portion (not shown) in the instrument panel at the driver's seat. Further, the ECU 25 stores abnormality information (abnormal code or the like) into a re-writable non-volatile memory, such as a backup RAM (not shown) of the ECU 25. The non-volatile memory is equivalent to a re-writable memory that holds stored data even when the power supply of the ECU 25 is OFF.

When an abnormality (for example, a failure) occurs in the constant current circuit 27, and when the constant current circuit 27 is controlled to stop the constant current Ics flowing between the sensor electrodes 33 and 34 of the oxygen sensor 21, an output of the oxygen sensor 21 differs from a normal output. In the present embodiment, an abnormality diagnosis to determine the presence or absence of an abnormality in the constant current circuit 27 is executed depending on whether an output of the oxygen sensor 21 is out of a predetermined normal range when the constant current circuit 27 is controlled to stop the constant current Ics. Hence, the presence or absence of an abnormality in the constant current circuit 27 can be determined with accuracy. Consequently, when an abnormality occurs in the constant current circuit 27, the abnormality can be detected promptly. Moreover, it is not necessary to switch the constant current Ics flowing between the sensor electrodes 33 and 34 when an abnormality diagnosis is executed. Hence, in comparison with a case where an abnormality diagnosis is executed on the basis of outputs of the oxygen sensor before and after the current value is switched, a time required for an abnormality diagnosis can be shorter. Accordingly, an abnormality diagnosis can be completed more frequently while the abnormality diagnosis executing condition is established. In addition, an adverse influence on other controls (for example, a rich injection control performed to neutralize the first catalyst 18 and the second catalyst 19 immediately after a fuel cut ends) can be prevented.

The present embodiment has described a system that controls the constant current circuit 27 to stop the constant current Ics before activation of the oxygen sensor 21. In the system, an output of the oxygen sensor 21 is stable in the vicinity of a reference value (for example, 0 V) before activation of the oxygen sensor 21 when the constant current circuit 27 is normal. Moreover, an abnormality diagnosis on the constant current circuit 27 can be executed on the basis of an output of the oxygen sensor 21 before activation of the oxygen sensor 21. Hence, an abnormality diagnosis on the constant current circuit 27 can be executed with accuracy before activation of the oxygen sensor 21. Further, an abnormality diagnosis on the constant current circuit 27 can be executed before activation of the oxygen sensor 21 and before a control on the basis of an output of the oxygen sensor 21 is started.

The present embodiment has described the system that controls the constant current circuit 27 to stop the constant current Ics during a fuel cut. In the system, an output of the oxygen sensor 21 is stable on the lean side (for example, in the vicinity of 0 V) during a fuel cut when the constant current circuit 27 is normal. Moreover, an abnormality diagnosis on the constant current circuit 27 is executed on the basis of an output of the oxygen sensor 21 during a fuel cut. Hence, an abnormality diagnosis on the constant current circuit 27 can be executed with accuracy during a fuel cut.

The present embodiment has described the system that controls the constant current circuit 27 to stop the constant current Ics after an engine stop. In the system, an output of the oxygen sensor 21 is stable on the lean side (for example, in the vicinity of 0 V) after an engine stop when the constant current circuit 27 is normal. Moreover, an abnormality diagnosis on the constant current circuit 27 is executed on the basis of an output of the oxygen sensor 21 after an engine stop. Hence, an abnormality diagnosis on the constant current circuit 27 can be executed with accuracy after an engine stop.

In the embodiment above, the present disclosure is applied to the system that controls the constant current circuit 27 to stop the constant current Ics during a fuel cut. It should be appreciated, however, that the present disclosure is not limited to the embodiment above. It may be configured in such a manner that the present disclosure is applied to a system that controls the constant current circuit 27 to maintain the constant current Ics at a predetermined value during a fuel cut to execute an abnormality diagnosis on the constant current circuit 27 on the basis of an output of the oxygen sensor 21 during a fuel cut. When configured as above, an abnormality diagnosis on the constant current circuit 27 can be executed during a fuel cut when the constant current circuit 27 is controlled to maintain the constant current Ics at a predetermined value. Even when configured as above, an output of the oxygen sensor 21 is stable on the lean side during a fuel cut when the constant current circuit 27 is normal. Hence, an abnormality diagnosis on the constant current circuit 27 can be executed with accuracy on the basis of an output of the oxygen sensor 21.

In the embodiment above, an abnormality diagnosis is executed in three periods before activation of the oxygen sensor 21, during a fuel cut, and after an engine stop. It should be appreciated, however, that the present disclosure is not limited to the configuration above. For example, an abnormality diagnosis may be executed in one or two of the periods before activation of the oxygen sensor 21, during a fuel cut, and after an engine stop. Further, the periods are not limited to the three periods specified above. An abnormality diagnosis on the constant current circuit 27 may be executed on the basis of an output of the oxygen sensor 21 when the constant current circuit 27 is controlled to stop the constant current Ics or when the constant current circuit 27 is controlled to maintain the constant current Ics at a predetermined value.

In the embodiment above, the constant current circuit 27 is connected to the atmosphere-side electrode layer 34 of the oxygen sensor 21 (sensor element 31). However, the present disclosure is not limited to the configuration above. For example, the constant current circuit 27 may be connected to the exhaust-side electrode layer 33 of the oxygen sensor 21 (sensor element 31) or the constant current circuit 27 may be connected to both of the atmosphere-side electrode layer 34 and the exhaust-side electrode layer 33.

In the embodiment above, the present disclosure is applied to the system using the oxygen sensor 21 having the sensor element 31 of a cup-like structure. However, the present disclosure is not limited to the configuration above. For example, the present disclosure may be applied to a system using an oxygen sensor having a sensor element of a lamination structure.

Further, the gas sensor is not limited to the oxygen sensor. For example, the present disclosure may be applied to gas sensors other than the oxygen sensor, such as an air-fuel ratio sensor that outputs a linear air-fuel ratio signal corresponding to an air-fuel ratio, an HC sensor that detects a concentration of HC, and an $NO_x$ sensor that detects a concentration of $NO_x$. Further, the present disclosure may be applied to gas sensors other than engine gas sensors.

While the present disclosure has been described with reference to the embodiments thereof, it is to be understood that the disclosure is not limited to the embodiments and constructions. The present disclosure is intended to cover various modification and equivalent arrangements. In addition, while the various combinations and configurations, which are preferred, other combinations and configurations, including more, less or only a single element, are also within the spirit and scope of the present disclosure.

The invention claimed is:

1. A gas sensor control device, comprising:
    a gas sensor that detects a concentration of a predetermined component contained in a detected gas using a sensor element in which a solid electrolyte body is disposed between a pair of sensor electrodes;
    a constant current supply portion that changes output characteristics of the gas sensor by controlling a constant current flowing between the sensor electrodes; and
    an abnormality diagnosis portion that executes an abnormality diagnosis to determine presence or absence of an abnormality in the constant current supply portion on the basis of an output of the gas sensor when the constant current supply portion is controlled to stop the constant current or maintain the constant current at a predetermined value.

2. The gas sensor control device according to claim 1, wherein:
    the abnormality diagnosis portion determines the presence or absence of an abnormality in the constant current supply portion depending on whether an output of the gas sensor is out of a predetermined normal range.

3. The gas sensor control device according to claim 1, further comprising:
    a constant current control portion that controls the constant current supply portion to stop the constant current until the gas sensor becomes active,
    wherein the abnormality diagnosis portion executes the abnormality diagnosis before the gas sensor becomes active.

4. The gas sensor control device according to claim 1, wherein:
    the gas sensor is a sensor that detects an air-fuel ratio of an emission gas of an internal combustion engine or whether the emission gas is rich or lean.

5. The gas sensor control device according to claim 4, further comprising:
    a constant current control portion that controls the constant current supply portion to stop the constant current or maintain the constant current at the predetermined value during a fuel cut executed to stop fuel injection of the internal combustion engine,
    wherein the abnormality diagnosis portion executes the abnormality diagnosis during the fuel cut.

6. The gas sensor control device according to claim 4, further comprising:
    a constant current control portion that controls the constant current supply portion to stop the constant current after the internal combustion engine stops,
    wherein the abnormality diagnosis portion executes the abnormality diagnosis after the internal combustion engine stops.

7. The gas sensor control device according to claim 1, wherein:
    the abnormality diagnosis portion is configured to execute the abnormality diagnosis without changing a direction of the constant current.

8. The gas sensor control device according to claim 1, wherein:
 the abnormality diagnosis portion is configured to execute the abnormality diagnosis to determine the presence or absence of the abnormality in the constant current supply portion on the basis of an output of the gas sensor when the constant current supply portion is controlled to stop the constant current.

9. The gas sensor control device according to claim 1, wherein:
 an abnormality diagnosis portion sets an abnormality flag to ON in order to provide a warning upon determination of the abnormality in the constant current supply portion.

\* \* \* \* \*